United States Patent
Park

(10) Patent No.: US 10,576,024 B2
(45) Date of Patent: Mar. 3, 2020

(54) MAKEUP COSMETIC COMPOSITION CONTAINING MULTIPLE COMPOSITE POWDER

(71) Applicant: Amorepacific Corporation, Seoul (KR)

(72) Inventor: Se Jun Park, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 15/740,398

(22) PCT Filed: Jun. 30, 2016

(86) PCT No.: PCT/KR2016/007070
§ 371 (c)(1),
(2) Date: Dec. 28, 2017

(87) PCT Pub. No.: WO2017/003234
PCT Pub. Date: Jan. 5, 2017

(65) Prior Publication Data
US 2018/0177686 A1 Jun. 28, 2018

(30) Foreign Application Priority Data

Jun. 30, 2015 (KR) .................. 10-2015-0093768

(51) Int. Cl.
*A61K 8/02* (2006.01)
*A61K 8/26* (2006.01)
*A61K 8/29* (2006.01)
*A61Q 1/12* (2006.01)

(52) U.S. Cl.
CPC ............ *A61K 8/022* (2013.01); *A61K 8/0245* (2013.01); *A61K 8/0254* (2013.01); *A61K 8/26* (2013.01); *A61K 8/29* (2013.01); *A61Q 1/12* (2013.01); *A61K 2800/412* (2013.01); *A61K 2800/42* (2013.01); *A61K 2800/591* (2013.01); *A61K 2800/621* (2013.01)

(58) Field of Classification Search
CPC combination set(s) only.
See application file for complete search history.

(56) References Cited

U.S. PATENT DOCUMENTS

| 4,623,396 A * | 11/1986 | Kimura | A61K 8/29 106/417 |
| 6,117,435 A | 9/2000 | Painter et al. | |
| 2011/0256194 A1 | 10/2011 | Misaki et al. | |
| 2012/0321684 A1* | 12/2012 | Maderazzo | A61K 8/19 424/401 |

FOREIGN PATENT DOCUMENTS

| EP | 1 366 737 A1 | 3/2003 |
| JP | 2008-37780 A | 2/2008 |
| KR | 10-0486442 B1 | 4/2005 |

OTHER PUBLICATIONS

International Search Report for PCT/KR2016/007070, dated Oct. 14, 2016 (PCT/ISA/210).

* cited by examiner

*Primary Examiner* — Audrea B Coniglio
(74) *Attorney, Agent, or Firm* — Sughrue Mion, PLLC

(57) ABSTRACT

A makeup cosmetic composition contains a first composite powder and a second composite powder, wherein the first composite powder and the second composite powder are plate-like powders coated in a coating layer. The first composite powder contains a coating layer having an average thickness of 20 to 70 nm, and the second composite powder contains a coating layer having an average thickness of 74 to 104 nm.

7 Claims, 4 Drawing Sheets

[FIG. 1]
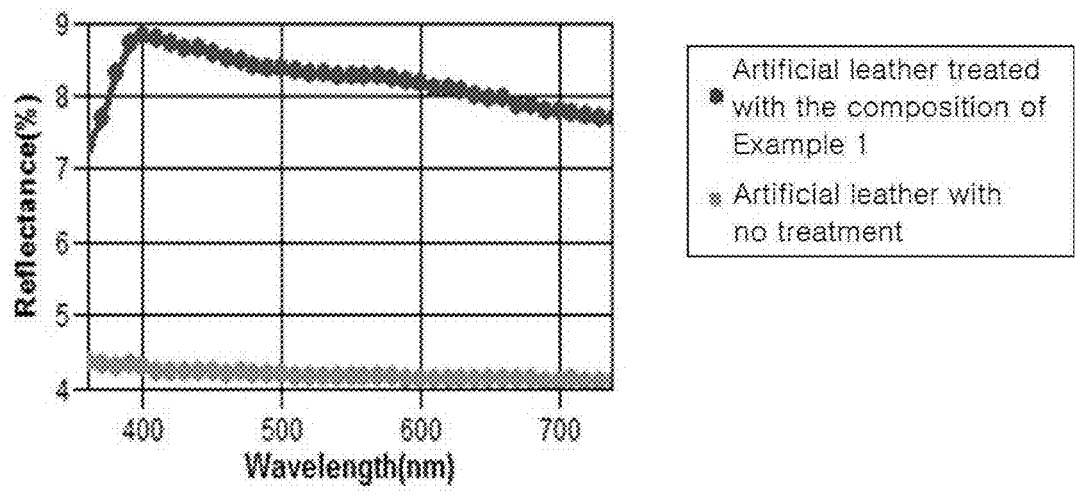
[FIG. 2]
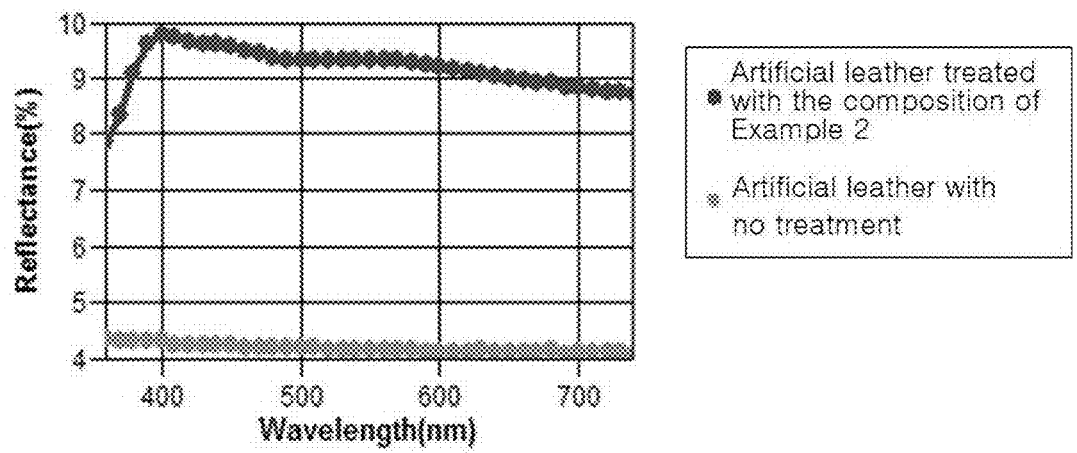

[FIG. 3]
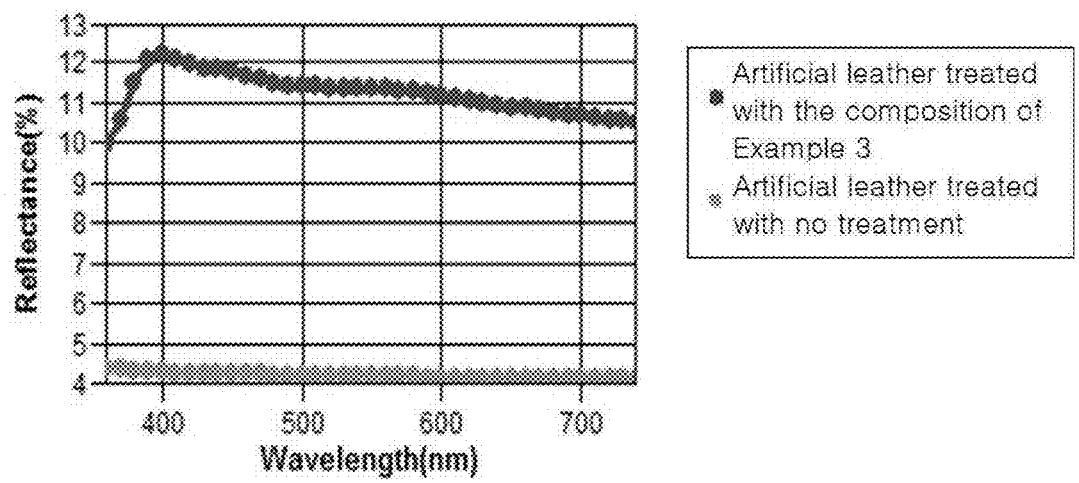
[FIG. 4]
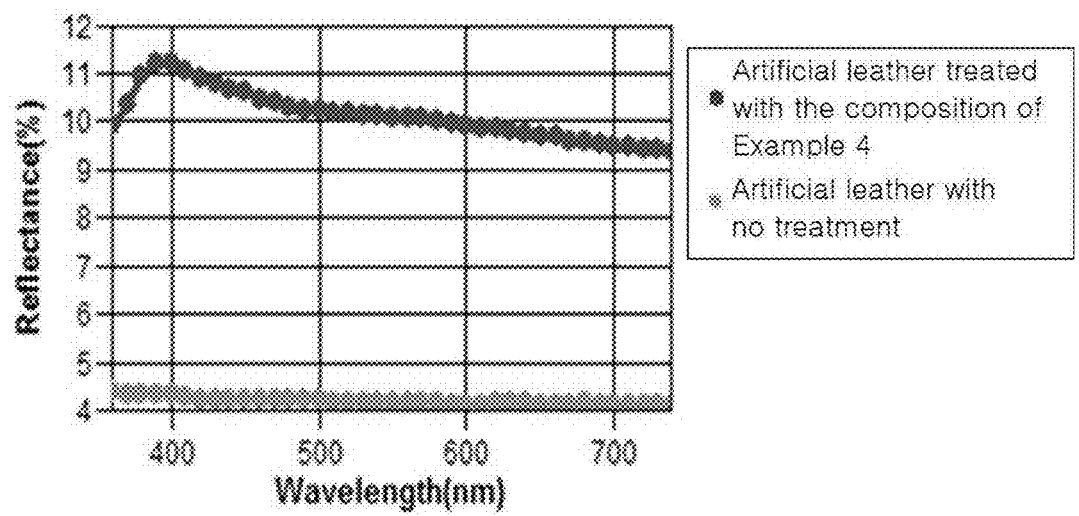

[FIG. 5]
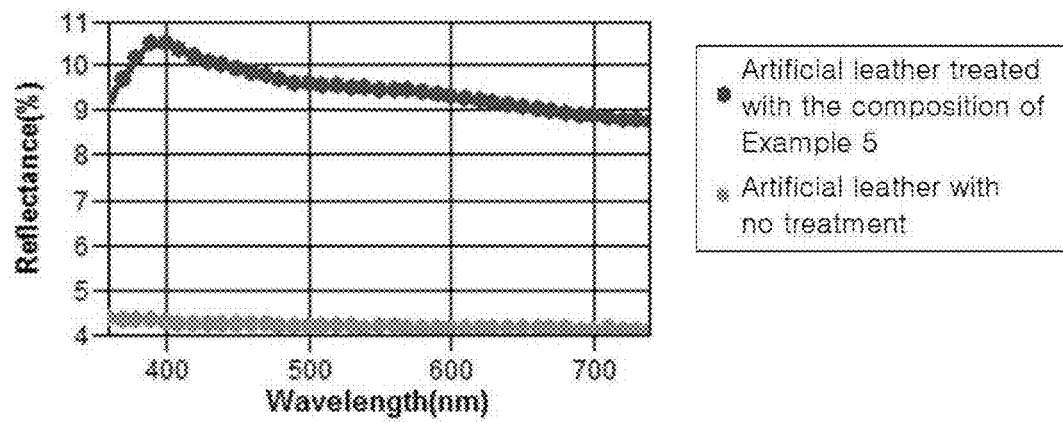
[FIG. 6]
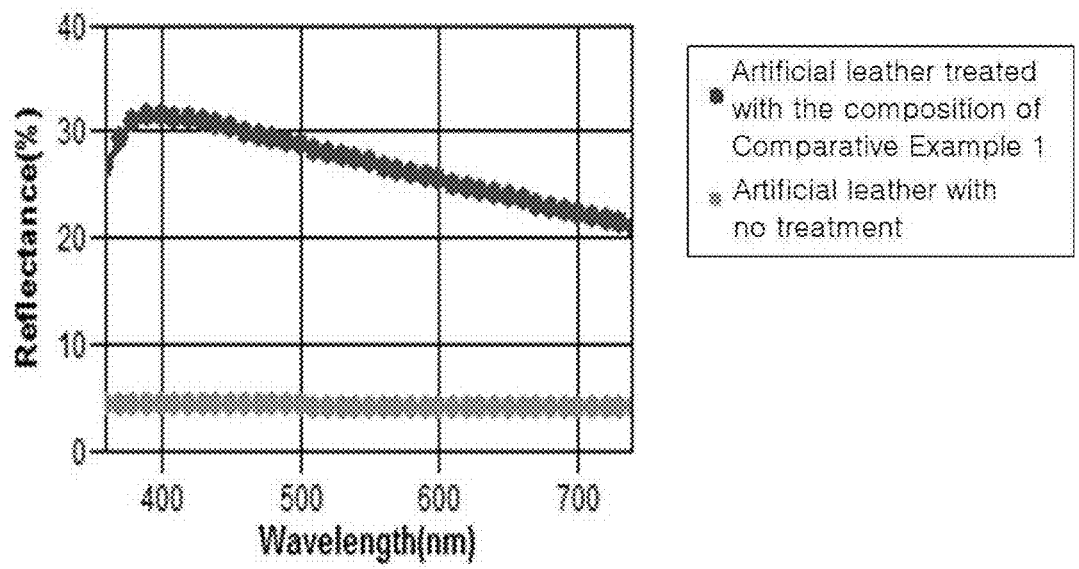

[FIG. 7]
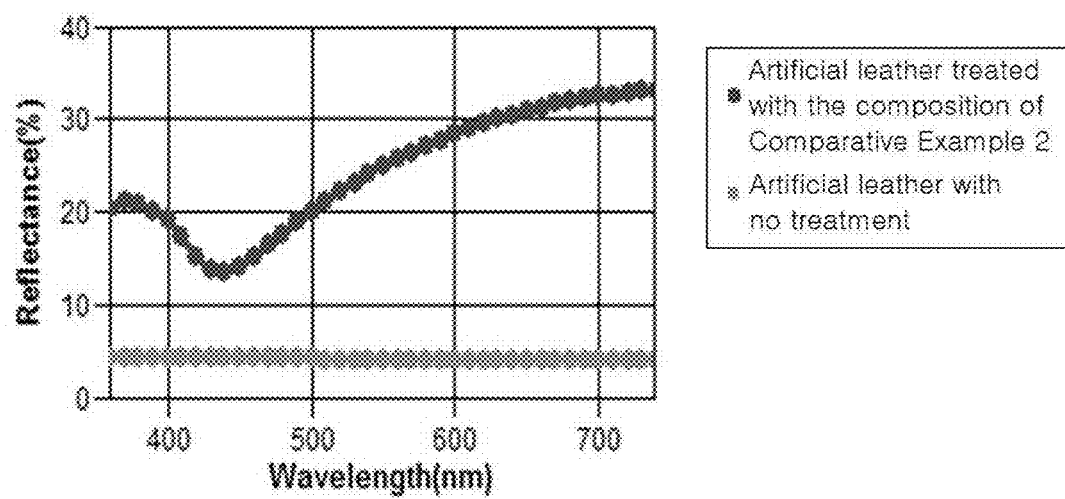

MAKEUP COSMETIC COMPOSITION CONTAINING MULTIPLE COMPOSITE POWDER

CROSS REFERENCE TO RELATED APPLICATIONS

This application is a National Stage of International Application No. PCT/KR2016/007070 filed Jun. 30, 2016, which claims the benefit of priority to Korean Patent Application No. 10-2015-0093768 filed on Jun. 30, 2015 with the Korean Intellectual Property Office, the disclosures of which are incorporated herein by reference in their entireties.

TECHNICAL FIELD

The present invention relates to a makeup cosmetic composition containing multiple composite powder.

BACKGROUND ART

Conventionally, in order to impart shininess and glossiness to the skin, a pearl pigment, which is a composite powder exhibiting colors caused by an interference effect or by a pigment, has been widely used by coating a plate-like powder such as a mica having a high reflectance of light with titanium dioxide, iron oxide, organic pigment or the like.

A makeup cosmetic composition containing such a pearl pigment can impart shininess or glossiness, but in general, due to the size of composite powder having a diameter of 20 µm or higher, it gives an unnatural glossiness when used in a large amount, and it has a disadvantage in that the skin gets oily over time which acts as a negative factor.

Meanwhile, a white light may be implemented by mixing each powder reflecting four colors. In this case, due to the interference effect of light, each light may be reinforced to impart a whitening effect, but in general, the natural whitening effect is deteriorated due to the mixing of composite powders having a diameter of 20 µm or higher, thereby deteriorating the whitening effect to some extent.

Further, although a makeup cosmetic composition containing the pearl pigment coated with titanium oxide can implement a white reflected light by adjusting the coated thickness, the reflected light, when applied to the skin, has a relatively high reflectance in the wavelength of 400 to 500 nm, and thus, there is a side effect that an unnatural whitening effect appears due to the reflected light having an emphasis on the blue light even when the skin tone brightens.

Furthermore, even in case of implementing a bright skin by titanium dioxide, which is commonly used in the art, an unnatural whitening effect appears due to the effect that the white light and blue light simultaneously appear.

Accordingly, there is a need for the development of makeup cosmetics capable of implementing a natural whitening effect.

DETAILED DESCRIPTION OF THE INVENTION

Technical Problem

It is an object of the present invention to provide a makeup cosmetic, which exhibits a uniform reflectance throughout the wavelength band of visible light just as a natural white light, while exhibiting an excellent whitening effect that brightens the skin tone, thereby reflecting the natural white light when applied to skin, that is, a makeup cosmetic composition implementing a light-whitening effect.

Technical Solution

The present invention provides a makeup cosmetic composition containing a first composite powder and a second composite powder.

Specifically, the present invention provides a makeup cosmetic composition, wherein the first composite powder and the second composite powder are plate-like powders coated in a coating layer, the first composite powder comprises a coating layer having an average thickness of 20 to 70 nm, and the second composite powder comprises a coating layer having an average thickness of 74 to 104 nm.

Advantageous Effects

The present invention can provide a makeup cosmetic composition in which the second composite powder reinforces the wavelength range exhibiting a relatively low reflectance in the first composite powder, while the first composite exhibiting a relatively high reflectance in the blue-based wavelength range brightens the skin tone, and consequently implementing a light-whitening effect, which exhibits a uniform reflectance in all visible light wavelength ranges, along with an excellent effect in improving the skin tone.

BRIEF DESCRIPTION OF DRAWINGS

In FIG. 1, the bottom line shows the measurement results with no treatment on the black artificial leather, and the upper line shows the results of measuring the reflected light after coating the composition of Example 1 onto the black artificial leather.

In FIG. 2, the bottom line shows the measurement results with no treatment on the black artificial leather, and the upper line shows the results of measuring the reflected light after coating the composition of Example 2 onto the black artificial leather.

In FIG. 3, the bottom line shows the measurement results with no treatment on the black artificial leather, and the upper line shows the results of measuring the reflected light after coating the composition of Example 3 onto the black artificial leather.

In FIG. 4, the bottom line shows the measurement results with no treatment on the black artificial leather, and the upper line shows the results of measuring the reflected light after coating the composition of Example 4 onto the black artificial leather.

In FIG. 5, the bottom line shows the measurement results with no treatment on the black artificial leather, and the upper line shows the results of measuring the reflected light after coating the composition of Example 5 onto the black artificial leather.

In FIG. 6, the bottom line shows the measurement results with no treatment on the black artificial leather, and the upper line shows the results of measuring the reflected light after coating the composition of Comparative Example 1 onto the black artificial leather.

In FIG. 7, the bottom line shows the measurement results with no treatment on the black artificial leather, and the upper line shows the results of measuring the reflected light after coating the composition of Comparative Example 2 onto the black artificial leather.

In FIGS. 1 to 7, the horizontal axis represents the wavelength band (unit: nm) of the reflected light, and the vertical axis represents the 7 reflectance (unit: %) of the corresponding wavelength band.

DETAILED DESCRIPTION OF THE EMBODIMENTS

The present invention provides a makeup cosmetic composition containing a first composite powder and a second composite powder.

In the present invention, the first composite powder is a plate-like powder coated in a coating layer, and the second composite powder is a plate-like powder coated onto a coating layer. The plate-like powders coated onto the coating layers of the first composite powder and the second composite powder are interpreted as having the same meaning, unless otherwise defined in the present specification.

The first composite powder according to the present invention includes a coating layer having an average thickness of 20 to 70 nm.

The second composite powder includes a coating layer having an average thickness of 74 to 104 nm.

In one embodiment of the present invention, the coating layer of the plate-like powders is titanium dioxide.

Titanium dioxide is a white pigment and an only component showing a refractive index of 2.5 to 2.7, and exhibits an effect of reflecting light when titanium dioxide is uniformly coated onto powder, thereby implementing a light-whitening effect. When the titanium dioxide is compared to zinc oxide, which is another white pigment, zinc oxide has a high refractive index of 1.9 to 2.0, but it has superior covering-ability to mask skin defects as it reflects more light.

In one embodiment of the present invention, the plate-like powder may be at least one selected from the group consisting of mica, synthetic mica, alumina, boron nitride powder, talc and sericite. As the difference between the refractive index of a coating layer and the refractive index of a plate-like powder increases, the light reflection effect is higher. Therefore, the plate-like powder is preferably mica having a lowest refractive index of 1.65.

In one embodiment of the present invention, the average particle diameter of the first composite powder or the second composite powder is 1 to 17 μm. If the average particle diameter of the first composite powder or the second composite powder is less than 1 μm, the glossy effect is insignificant. Further, if the average particle diameter exceeds 17 μm, there is a problem that the applicability, uniformity and moldability are deteriorated when the powder is used in a twin-cake formulation, which is a compressed powder formulation. In addition, the glossiness may be expressed as the content thereof increases, but may be unnaturally expressed or may get smeared, and thus showing a limited glossy effect. In contrast, if the average particle diameter of the first composite powder and the second composite powder is within the range of 1 to 17 μm, a natural glossiness can be expressed due to an interference light.

In one embodiment of the present invention, the content of the first composite powder is 5 to 25% by weight based on the total weight of the composition.

If the content of the first composite powder is less than 5% by weight, the effect of reflecting light is insignificant and thus the light-whitening effect may not be exhibited. If the content of the first composite powder exceeds 25% by weight, the reflected light is expressed as having too much white, resulting in an unnatural effect.

In one embodiment of the present invention, the content of the second composite powder is 2 to 10% by weight based on the total weight of the composition.

If the content of the second composite powder is less than 2% by weight, the reflected light of the second composite powder has an insignificant effect to offset the blue light of the first composite powder, resulting in an unnatural light-whitening effect. If the content thereof exceeds 10% by weight, even when the reflected light of the second composite powder offsets the blue light of the first composite powder, the yellow reflected light of the second composite powder appears strongly, and as a result, it is not possible to exhibit the light-whitening effect to be implemented in the present invention due to the bright yellow reflected light.

In one embodiment of the present invention, the weight ratio of the first composite powder to the second composite powder is greater than or equal to 4:1 and less than 3:1, more preferably, greater than or equal to 3.8:1 and less than or equal to 3.3:1.

If the weight ratio of the first composite powder to the second composite powder is less than 4:1, the white reflected light and the blue reflected light occur simultaneously, and thus the reflected light may be unnatural. If the weight ratio is greater than or equal to 3:1, the white reflected light and the yellow reflected light occur simultaneously, and thus it becomes not possible to exhibit the light-whitening effect to be achieved in the present invention.

In one embodiment of the present invention, the makeup cosmetic composition has a lightness (L) of 58.3 to 58.4 in the CIELAB color system using a color-difference meter and satisfies the color coordination in which the a*, which is the X-axis of saturation coordinate, is −0.8 to −0.5 and the b*, which is the Y-axis of saturation coordinate, is −0.3 to 0.6 at the same time.

In one embodiment of the present invention, the makeup cosmetic composition is for light-whitening.

In the present specification, the light-whitening means that when the composition is applied to the skin, the reflected light reflected from the composition exhibits a uniform reflectance in all visible light wavelength bands, while increasing the brightness of the skin.

Further, the light-whitening exhibits an effect that can perceive an increase in shininess and glossiness when perceived by the human eye.

The makeup cosmetic composition of the present invention is not limited to its formulations, and may be formulated in the form of, for example, a makeup primer, a foundation, a blemish balm cream, a makeup base, a two-way cake, a compact, a powder or an eye shadow, etc.

Hereinafter, the present invention will be described in more detail by way of Examples. However, these Examples are given for illustrative purposes only, and the scope of the invention is not intended to be limited by these Examples.

[Reference Example 1] Measurement of Color Coordinate of the First Composite Powder 0.002 g of Flamenco® Ultra Silk 2500 (trade name) manufactured by BASF (coating thickness of titanium dioxide: 43 to 60 nm) corresponding to the first composite powder according to the present invention was coated onto a black artificial leather having a size of 7.5 cm×2.5 cm, and the values according to the CIELAB color system were measured using a color-difference meter, Spectrophotometer CM-5 (trade name) manufactured by KONICA MINOLTA.

As a result of the measurements, the lightness (L) was measured to be 58.87, the a*, which is the X-axis of saturation coordinate, was measured to be −1.64, and the b*, which is the Y-axis of saturation coordinate was measured to be −4.91.

[Reference Example 2] Measurement of Color Coordinate of the Second Composite Powder 0.002 g of Flamenco® Silk Gold 230M (trade name) manufactured by BASF (coating thickness of titanium dioxide: 60 to 84 nm) corresponding to the second composite powder according to the present invention was coated onto a black artificial leather having a size of 7.5 cm×2.5 cm, and the values according to the CIELAB color system were measured using a color-difference meter, Spectrophotometer CM-5 (trade name) manufactured by KONICA MINOLTA.

As a result of the measurements, the lightness (L) was measured to be 56.5, a*, which is the X-axis of saturation coordinate, was measured to be 2.94, and b*, which is the Y-axis of saturation coordinate was measured to be 17.95.

[Reference Example 3] Preparation of Examples and Comparative Examples

The compositions of Examples 1 to 5 and Comparative Examples 1 and 2 were prepared in the form of mixed powder by the composition (unit: wt %) shown in Table 1 below.

TABLE 1

| Components | Example 1 | Example 2 | Example 3 | Example 4 | Example 5 | Comparative Example 1 | Comparative Example 2 |
|---|---|---|---|---|---|---|---|
| First composite powder | 85 | 80 | 78 | 75 | 70 | 10 | — |
| Second composite powder | 15 | 20 | 22 | 25 | 30 | — | 10 |
| Weight ratio of first composite powder:second composite powder | 5.667:1 | 4.000:1 | 3.545:1 | 3.000:1 | 2.333:1 | — | — |

[Experimental Example 1] Measurement and Comparison of Color Coordination 0.003 g of each composition of Examples 1 to 5 and Comparative Examples 1 and 2 prepared according to Reference Example 3 was coated onto a black artificial leather having a size of 7.5 cm×2.5 cm, and the values according to the CIELAB color system were measured using a color-difference meter, Spectrophotometer CM-5 (trade name) manufactured by KONICA MINOLTA. The results are shown in Table 2 below.

TABLE 2

| | Example 1 | Example 2 | Example 3 | Example 4 | Example 5 | Comparative Example 1 | Comparative Example 2 |
|---|---|---|---|---|---|---|---|
| L | 34.5 | 36.51 | 40.11 | 37.97 | 36.83 | 58.87 | 56.5 |
| a* | −0.12 | −0.07 | −0.1 | −0.06 | −0.09 | −1.64 | 2.94 |
| b* | −1.01 | −0.77 | −1.17 | −1.46 | −1.43 | −4.91 | 17.95 |

[Experimental Example 2] Measurement and Comparison of Visible Light Wavelength 0.003 g of each composition of Examples 1 to 5 and Comparative Examples 1 and 2 prepared according to Reference Example 3 was coated onto a black artificial leather having a size of 7.5 cm×2.5 cm, and then the reflectance according to the visible light wavelength band of 400 nm to 700 nm was measured using a measuring device, Spectrophotometer CM-5 (trade name) manufactured by KONICA MINOLTA. The results are shown in FIGS. 1 to 7. Further, the value difference between the maximum value and the minimum value of the reflectance in the wavelength range of 400 nm to 700 nm is shown in Table 3 below.

TABLE 3

| | Example 1 | Example 2 | Example 3 | Example 4 | Example 5 | Comparative Example 1 | Comparative Example 2 |
|---|---|---|---|---|---|---|---|
| Value difference between | 1 | 1 | 1.4 | 1.8 | 1.7 | 9 | 19 |

TABLE 3-continued

|  | Example 1 | Example 2 | Example 3 | Example 4 | Example 5 | Comparative Example 1 | Comparative Example 2 |
|---|---|---|---|---|---|---|---|
| the maximum and minimum of the reflectance in the wavelength range of 400 nm to 700 nm (%) |  |  |  |  |  |  |  |

In FIGS. 6 and 7, it was confirmed that the composition of Comparative Example 1 mainly increased the reflectance in the wavelength band of 400 to 500 nm, that is, the blue-based wavelength band, whereas the composition of Comparative Example 2 mainly increased the reflectance in the wavelength range of 600 to 700 nm, that is the yellow-based wavelength range, and that the value difference between the maximum and minimum of the reflectance in the wavelength range of 400 nm to 700 nm was 9% or higher, which is a significant difference.

In contrast, in FIGS. 1 to 5, it was confirmed that the compositions of Examples 1 to 5 uniformly increased the reflectance in all visible light wavelength bands and thus exhibited a natural white light, that is, a light-whitening effect. In particular, as shown in FIGS. 1 to 5 and the Tables 2 and 3 above, it was confirmed that the compositions of Examples 2 and 3 exhibited an excellent light-whitening effect due to high brightness, while uniformly increasing the reflectance in all visible light wavelength ranges.

[Experimental Example 3] Evaluation on Feeling of Use by Panels

Tween cake compositions in the form of a compressed powder according to Formulation Example 1 and Comparative Formulation Examples 1 to 3 were prepared according to a conventional method by the compositions shown in Table 4 below.

TABLE 4

| Components | Formulation Example 1 | Comparative Formulation Example 1 | Comparative Formulation Example 2 | Comparative Formulation Example 3 |
|---|---|---|---|---|
| Talc | to 100 | to 100 | to 100 | to 100 |
| sericite | 20.0 | 20.0 | 20.0 | 20.0 |
| Silica | 10.0 | 10.0 | 10.0 | 10.0 |
| Titanium dioxide | 12.0 | 12.0 | 12.0 | 22.0 |
| Zinc oxide | 3.0 | 3.0 | 3.0 | 3.0 |
| First composite powder | 7.8 | 10.0 | — | — |
| Second composite powder | 2.2 | — | 10.0 | — |
| Iron oxide | 2.0 | 2.0 | 2.0 | 2.0 |
| Mineral oil | 7.0 | 7.0 | 7.0 | 7.0 |

20 female consumer panelists in 20s to 30s directly coated test materials onto their own face, and evaluated the feeling of use in terms of naturalness, shininess, pore coverage and glossiness for Formulation Example 1 and Comparative Formulation Examples 1 to 3. The sonsory evaluation thereof was performed before and after actual coating, and compared. The results are shown in Table 5 below.

TABLE 5

| Test materials | Expression of natural light whitening | Shininess | Pore coverage | Glossiness |
|---|---|---|---|---|
| Formulation Example 1 | ⊚ | ○ | ○ | ○ |
| Comparative Formulation Example 1 | ○ | ○ | ○ | ○ |
| Comparative Formulation Example 2 | ○ | ○ | ○ | ○ |
| Comparative Formulation Example 3 | Δ | X | ○ | X |

⊚: Excellent,
○: Good,
Δ: Moderate,
X: Poor

As shown in Table 5 above, it was confirmed that the Formulation Example 1 showed higher glossiness and shininess compared to those of Comparative Formulation Example 3, and it naturally showed an excellent whitening effect caused by light compared to Comparative Formulation Examples 1 and 2. Accordingly, it can be seen that the composition according to the present invention showed an effect in bringing a natural and bright skin expression after coating it onto the skin, due to a small difference in spectrum.

The invention claimed is:

1. A makeup cosmetic composition containing a first composite powder and a second composite powder,
    wherein the first composite powder and the second composite powder are plate-like powders,
    wherein the first composite powder comprises a coating layer having an average thickness of 20 to 70 nm,
    wherein the second composite powder comprises a coating layer having an average thickness of 74 to 104 nm,
    wherein a weight ratio of the first composite powder to the second composite powder is 5.667 to 3.545:1,
    wherein the content of the first composite powder is 5 to 25% by weight based on the total weight of the composition, and
    wherein the content of the second composite powder is 2 to 10% by weight based on the total weight of the composition.

2. The makeup cosmetic composition of claim 1, wherein the coating layer of the plate-like powders is titanium dioxide.

3. The makeup cosmetic composition of claim 1, wherein each of the first composite powder and the second composite powder are at least one selected from the group consisting of mica, synthetic mica, alumina, boron nitride powder, talc, and sericite.

4. The makeup cosmetic composition of claim 1, wherein an average particle diameter of the first composite powder or the second composite powder is 1 to 17 μm.

5. The makeup cosmetic composition of claim 1, wherein the makeup cosmetic composition has a brightness (L) of 58.3 to 58.4 in the CIELAB color system using a color-difference meter and satisfies the color coordination in which the a*, which is the X-axis of saturation coordinate, is −0.8 to −0.5 and the b*, which is the Y-axis of saturation coordinate, is −0.3 to 0.6 at the same time.

6. The makeup cosmetic composition of claim 1, which has a light-whitening effect.

7. The makeup cosmetic composition of claim 1, wherein a weight ratio of the first composite powder to the second composite powder is 5.667 to 4:1.

* * * * *